(12) United States Patent
Goldau

(10) Patent No.: US 6,187,199 B1
(45) Date of Patent: Feb. 13, 2001

(54) PROCESS AND DEVICE FOR DETERMINING HEMODIALYSIS PARAMETERS

(75) Inventor: Rainer Goldau, Werneck (DE)

(73) Assignee: Fresenius Medical Care Deutschland GmbH, Bad Homburg (DE)

(*) Notice: Under 35 U.S.C. 154(b), the term of this patent shall be extended for 0 days.

(21) Appl. No.: 09/155,276
(22) PCT Filed: Jan. 22, 1998
(86) PCT No.: PCT/EP98/00326
§ 371 Date: Apr. 26, 1999
§ 102(e) Date: Apr. 26, 1999
(87) PCT Pub. No.: WO98/32476
PCT Pub. Date: Jul. 30, 1998

(30) Foreign Application Priority Data

Jan. 24, 1997 (DE) .............................................. 197 02 442

(51) Int. Cl.$^7$ .................................................. B01D 61/30
(52) U.S. Cl. ...................... 210/646; 73/61.41; 210/93; 210/96.2; 210/739; 436/79; 436/147; 436/150
(58) Field of Search ............................... 210/85, 94, 96.1, 210/96.2, 143, 149, 175, 321.71, 646, 647, 739, 745, 746, 93, 742; 604/4.01, 5.01, 6.01, 6.11, 6.14; 73/61.41; 436/79, 147, 150

(56) References Cited

U.S. PATENT DOCUMENTS

| | | | |
|---|---|---|---|
| 4,508,622 | * | 4/1985 | Polascegg et al. .................. 210/96.2 |
| 5,100,554 | * | 3/1992 | Polaschegg .......................... 210/96.2 |
| 5,567,320 | * | 10/1996 | Goux et al. .......................... 210/96.2 |
| 5,792,367 | * | 8/1998 | Mattesson et al. ................... 210/646 |
| 5,938,938 | * | 8/1999 | Bosetto et al. ....................... 210/646 |

FOREIGN PATENT DOCUMENTS

| | | |
|---|---|---|
| 0 291 421 A1 | 11/1988 | (EP) . |
| 0 428 927 A1 | 5/1991 | (EP) . |
| 0 528 437 A1 | 2/1993 | (EP) . |
| 0 532 433 A1 | 3/1993 | (EP) . |
| 0 547 025 A1 | 6/1993 | (EP) . |
| 0 658 352 A1 | 6/1995 | (EP) . |

* cited by examiner

Primary Examiner—Joseph W. Drodge
(74) Attorney, Agent, or Firm—Kenyon & Kenyon

(57) ABSTRACT

A method is described for determining hemodialysis parameters during an extracorporeal blood treatment according to which the blood to be treated in an extracorporeal circulation flows through the blood chamber of a dialyzer divided by a semipermeable membrane into the blood chamber and a dialysate chamber, and dialysate in a dialysate path flows through the dialysate chamber of the dialyzer. According to the method pursuant to the invention, the hemodialysis parameter can also be determined when no balanced state has yet been established. The method according to the invention is based on the response of the dialyzer to a pulse function as inlet signal (pulse response) from the course over time of the physical or chemical characteristic quantity of the dialysate upstream and downstream of the dialyzer. The hemodynamic parameter is then determined from the pulse response of the dialyzer.

24 Claims, 2 Drawing Sheets

PROCESS AND DEVICE FOR DETERMINING HEMODIALYSIS PARAMETERS

This application is a 371 of PCT/EP98/00326, filed Jan. 22, 1998.

FIELD OF THE INVENTION

The invention relates to a method of determining hemodialysis parameters during extracorporeal blood treatment and also a device with a component for determining hemodialysis parameters.

BACKGROUND OF THE INVENTION

An important function of human kidneys is the excretion from the blood of urine-bound substances and adjustment of water and electrolyte elimination. Hemodialysis is a treatment method designed to compensate for renal dysfunction in elimination of urine-bound products and adjustment of the electrolyte concentration in the blood.

During hemodialysis blood is directed to an extracorporeal circulation through the blood chamber of a dialyzer; the blood chamber is separated from a dialysate chamber by a semipermeable membrane. The dialysate chamber is fed with dialysate containing blood electrolytes in a specified concentration. The concentration of the dialysate (cd) corresponds to the blood concentration of a healthy person. During a treatment, the patient's blood and the dialysate are passed by both sides of the membrane, usually in countercurrent, at a predetermined flow rate (Qb or Qd). The urine-bound products diffuse through the membrane from the blood chamber to the dialysate chamber, while at the same time the electrolytes present in the blood and in the dialysate diffused from the chamber of higher concentration to the chamber of lower concentration. The metabolism can also be influenced by applying transmembrane pressure.

To be able to optimize the blood treatment method, hemodialysis parameters must be determined during the extracorporeal blood procedure (in vivo). One parameter of particular interest is the value for the efficiency exchange of the dialyzer, represented by the so-called "clearance" or "dialysance D."

Clearance for a specified substance K denotes the virtual (calculated) blood volume from which a specified substance is removed completely in the dialyzer per minute under defined conditions. Dialysance is another term for determining the efficiency of a dialyzer, which takes into account the concentration of the eliminated substance in the dialysate. In addition to these dialyzer performance parameters, other parameters are also important, such as the values of the aqueous portion of the blood, the blood volume and the concentration in the blood at the inlet, etc.

It is relatively complex to quantify blood purification methods mathematically on the basis of measurement technology and to determine the above-mentioned dialysis parameters. A basic measurement reference work in this regard is Sargent J. A., Gotch F. A.: Principles and Biophysics of Dialysis, in: W. Drukker, F. M. Parsons, J. F. Maher (eds.) *Replacement of Renal Function by Dialysis,* Nijhoff, The Hague 1983.

Dialysance or clearance for a given electrolyte, e.g., sodium, at the zero ultrafiltration rate is determined as follows. The dialysance D is equal to the ratio between the mass transport for this electrolyte on the blood side (Qb× (cbi–cbo)) and the difference in concentration of this electrolyte between the blood and the dialysate at the inlet of the dialyzer (cbi–cdi).

$$D = Qb \cdot \frac{cbi - cbo}{cbi - cdi} \quad (1)$$

On the basis of mass balance:

$$Qb \cdot (cbi-cbo) = -Qd \cdot (cdi-cdo) \quad (2)$$

It follows from equations (1) and (2) above that:

$$D = Qd \cdot \frac{cdi - cdo}{cbi - cdi} \quad (3)$$

where in (1) through (3):
Qb=effective blood flow
Qd=dialysate flow
cb=concentration of the substance in the blood
cd=concentration of the substance in the dialysate
i=dialyzer inlet
o=dialyzer outlet The effective blood flow is the flow of the blood portion in which the substances to be removed are dissolved, i.e., it is based on the (aqueous) solution volume for this substance. Depending on the substance, this may be the plasma water flow or the blood water flow, i.e., the total amount of water in whole blood.

The known methods of in-vivo determination of hemodialysis parameters are based on the above considerations. In this connection, an attempt is made to manage without a procedure of direct measurement of the blood side because this could represent a source of considerable risk. Therefore, the values that are to be determined must be derived solely from measurements on the dialysate side.

German Patent DE 39 38 662 C2 (European Patent EP 0 428 927 A1) describes a method of in-vivo determination of hemodialysis parameters by which the dialysate electrolyte transfer is measured at two different dialysate concentrations at the inlet. On the assumption that the concentration in the blood at the inlet is constant, dialysance can be determined according to the known method by determining the value of the differences in dialysate ion concentration at the inlet and outlet sides of the dialyzer at the time points of the first and second measurements, then by dividing this value by the difference in dialysate ion concentration at the inlet side at the times of the first and the second measurements and then multiplying by the dialysate flow. With this procedure, the relatively long measurement time proves to be a disadvantage, due to the fact that after the dialysate is adjusted to the new inlet concentration a stable steady-state condition must first be established at the dialyzer outlet before the new measurement value can be taken up. Depending on the system, it takes a certain time for a conductivity jump at the dialyzer inlet to lead to stable conditions at the dialyzer outlet.

In the article by Niels A. Lassen, Ole Henriksen, Per Sejrsen in the *Handbook of Physiology, The Cardiovascular System,* Vol. 3, "Peripheral Circulation and Organ Blood Flow," Part I, American Physiological Society, 1983, the response of an intracorporeal circulation to a bolus injection and subsequent measurement of the concentration is discussed in greater detail, whereby questions of signal convolution play an important part.

OBJECTS OF THE INVENTION

The object of the invention is to propose a method that permits the rapid determination of hemodialysis parameters during extracorporeal blood treatment. Another object of the invention is to create a device for carrying out the method.

This object is achieved using a method according to the invention, comprising determining the pulse response of a dialyzer to a pulse function, a change in the inlet level of a chemical or physical parameter, and utilizing the pulse response to determine hemodialysis parameters during dialysis treatment. The object of the invention is also achieved by a device that determines hemodialysis parameters during hemodialysis treatment using the pulse response of the dialyzer to a pulse function.

This object is achieved according to the invention through the characterizing features of the claims.

With the method according to the invention, a physical or chemical characteristic quantity or parameter of the dialysate, e.g., the concentration of a substance in the dialysate for determination of the dialysance D, is changed in the dialysate path upstream and then measured downstream from the dialyzer. The physical or chemical parameter in question should be adjusted to physiologically tenable values. If the course over time of the parameter change upstream of the dialyzer is not known, the parameter is also measured upstream of the dialyzer. Also included among the changeable physical or chemical characteristic quantities are the density, refractive index, conductivity, temperature or dialysate rate.

With the method according to the invention a hemodialysis parameter, e.g., the dialysance D, can also be determined when no balanced state has yet been established. Accordingly, only brief measurement times are required. Since the relatively long measurement times that are required with the known methods for determining hemodynamic parameters can lead to a systematic change in the hemodynamic parameters during the measurement, short measurement times are an advantage. Moreover, the method according to the invention also permits continuing measurements.

The method according to the invention is based on determination of the response of the dialyzer to the pulse function as inlet signal (pulse response) from the course over time of the physical or chemical characteristic quantity of the dialysate upstream and the course over time of the physical or chemical characteristic quantity downstream of the dialyzer. The hemodynamic parameter is then determined from the pulse response of the dialyzer.

The pulse response of the dialyzer can be determined at an optional course over time of the physical or chemical characteristic quantity upstream or downstream of the dialyzer. In principle, however, it is also possible to determine the pulse response with sufficient accuracy by measuring the course over time of the physical or chemical characteristic quantity downstream from the dialyzer in the case of a sufficiently sharp inlet pulse.

In a preferred embodiment of the invention, the hemodynamic parameter for determining the dialysance is obtained by determining the integral with respect to the pulse response of the dialyzer. The integral with respect to the pulse response is then compared with predetermined values characteristic of a given dialysance. The predetermined values can be obtained, for example, from the known methods from DE 39 38 662 C2 (EP 0 428 927 A1).

In another preferred embodiment of the invention, an effective measurement value is calculated with knowledge of the pulse response of the dialyzer at each outlet value that would have been measured with a stationary steady-state condition of the dialyzer inlet.

With the method according to the invention, the dynamic system is treated by calculation at every point in time as the equivalent stationary system. Accordingly, the characteristic quantities required for determination of the hemodialysis parameters can be obtained even when the stationary state has not yet been established.

The method according to the invention, as well as the device for carrying out that method, is described in greater detail below with reference to the figures.

BRIEF DESCRIPTION OF THE DRAWING

FIG. 2b shows the response of the dialyzer to the Gaussian signal of FIG. 2a.

DETAILED DESCRIPTION OF THE PREFERRED EMBODIMENT

Figure 1:
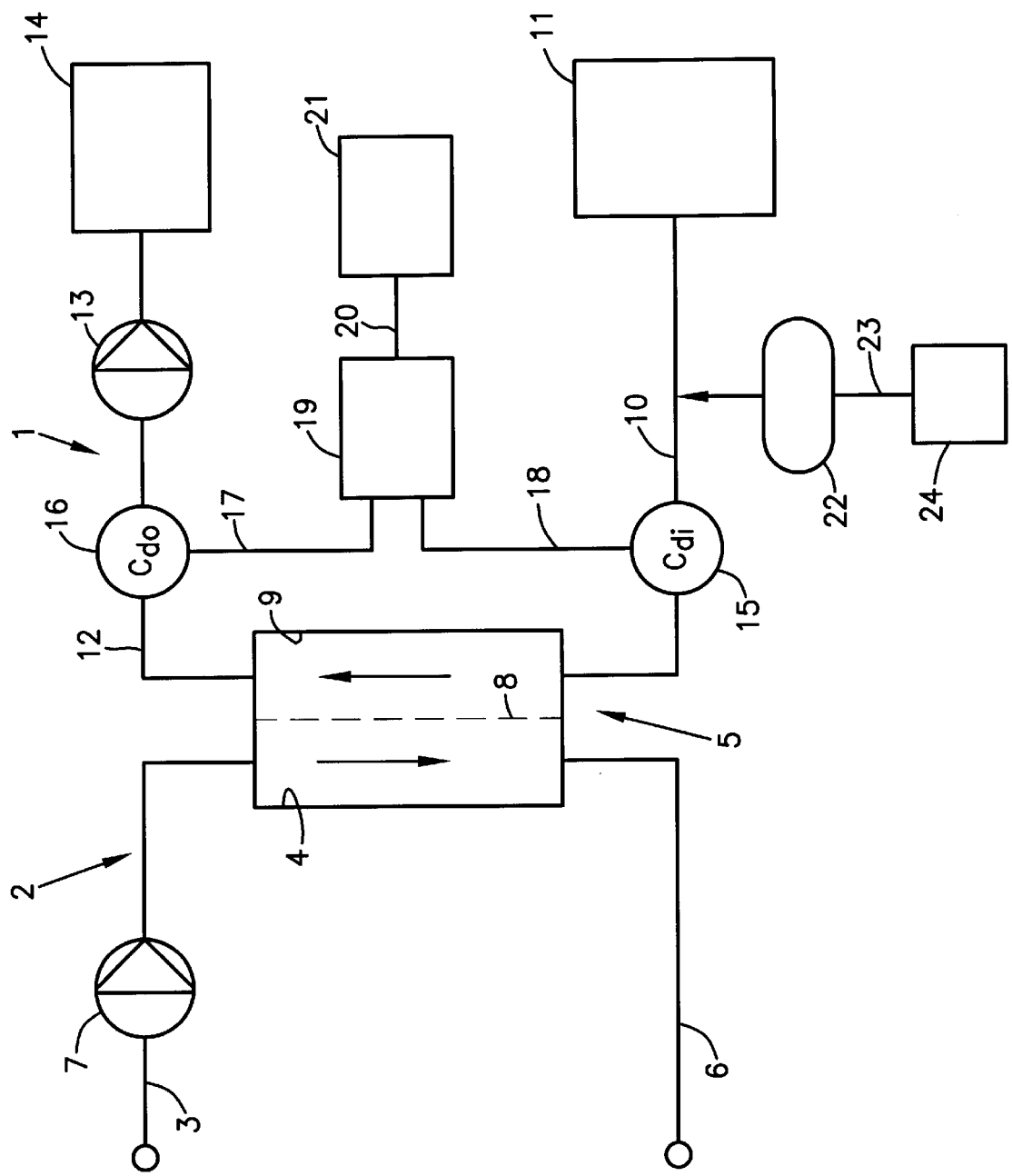
FIG. 1 shows a basic wiring diagram of the device according to the invention, with which the method according to the invention is carried out for the in vivo determination of hemodialysis parameters.

The device according to the invention for determining hemodialysis parameters can constitute a separate structural subgroup. But it can also be a component of a dialysis device, especially since some of the components of the device according to the invention are already available in known dialysis devices. The apparatus according to the invention is described below together with the key components of the dialysis device.

The dialysis device is composed essentially of a dialysate part 1 and an extracorporeal blood circulation 2. The extracorporeal blood circulation includes an arterial branch 3, the blood chamber 4 of the dialyzer 5 and a venous branch 6. In the arterial branch 3 a blood pump 7 is arranged which provides a preset blood flow rate in the extracorporeal circulation.

The dialysate chamber 9 of the dialyzer separated from the blood chamber 4 by a semipermeable membrane 8 is connected to a dialysate source 11 through a feed line 10. A drain line 12 to which a dialysate pump 13 is connected that sets the flow rate in the dialysate leads to a drain 14.

Provided in both the feed line 10 and the drain line 12 is a measuring arrangement 15, 16 for determining the ion concentration of the dialysate at the dialyzer inlet 5 and the substance concentration of the dialysate at the outlet of the dialyzer. The measuring arrangements 15, 16 for determining the dialysate inlet and outlet concentrations have conductivity sensors installed upstream and downstream from the dialyzer 5 which preferably measure the temperature-corrected conductivity of the dialysate on the basis of the Na concentration. Optical sensors for measuring the dialysate inlet or outlet concentration, respectively, can be arranged in the dialysate path, instead of the conductivity sensors. The conductivity sensors are connected to the storage unit 19 via data lines 17, 18. The storage unit 19 receives the data measured by the sensors and stores these in chronological sequence. The measured values are conveyed over a data line 20 to a computer and analyzer unit 21, which determines the hemodialysis parameters in a microprocessor from the data obtained. Such a microprocessor is usually already available in a dialysis apparatus.

To change the Na concentration of the dialysate in the dialysate path upstream from the dialyzer 5 an arrangement 22 is provided which is only shown schematically in FIG. 1.

By means of arrangement 22, the dialysate flowing in the dialyzer can be loaded with a concentrate bolus. The course of the measurement is controlled by a control unit 24 which is connected with the arrangement 22 via signal line 23 for loading the concentrate bolus.

When the temperature of the blood is to be determined as a hemodynamic parameter, temperature sensors rather than conductivity sensors are used which are arranged in the dialysate path upstream or downstream from the dialyzer 5. In this case, the arrangement 22 for changing the physical or chemical characteristic quantity in the dialysate path upstream from the dialyzer is a heating arrangement for producing a temperature surge.

The dialysate flows through the dialysate chamber 9 at a flow rate Qd preset by the rotational speed of the pump 13, and the inlet concentration cdi, that is variable by means of the arrangement 22, which is detected by means of the conductivity sensor 15 provided upstream. The outlet concentration cdo of the dialysate established during dialysis is detected by means of the conductivity sensor 16 provided downstream.

For a better understanding, the theoretical principles of the method for determining the hemodialysis parameters are explained in detail below.

Figure 2A:
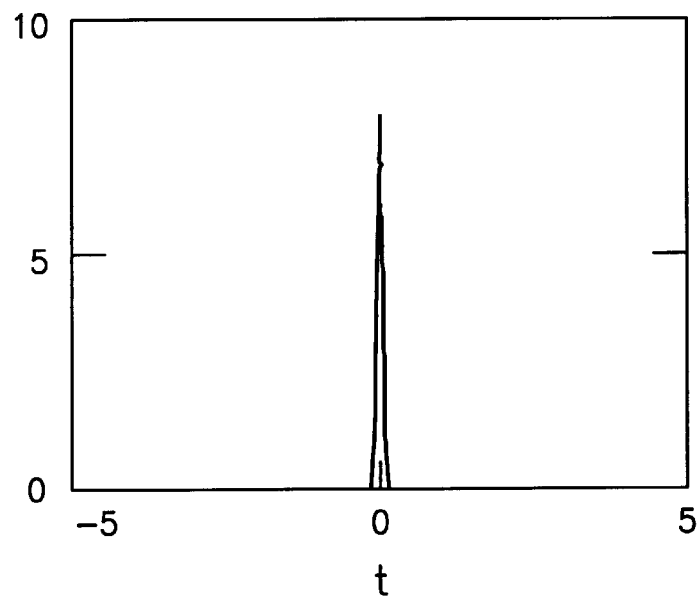
FIG. 2a shows a Gaussian signal as an example function for a change of the dialysate inlet concentration.

FIG. 2a shows an electrolyte concentration bolus at the inlet side of the dialyzer loaded at the point in time t=0. It is of short duration compared to the flow time of the dialysate through the dialyzer, with its baseline corresponding to the theoretical concentration of the electrolyte considered.

Figure 2B:
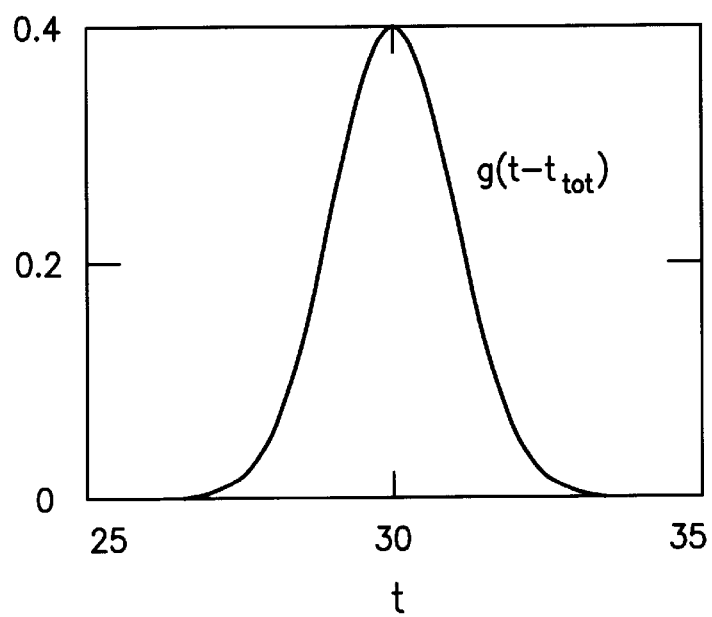

The concentrate bolus can be detected by conductivity measurement upstream and downstream of the dialyzer. The conductivity sensor 15 provided at the dialyzer inlet measures a liquid element dV which carries the conductivity pulse as a sharp pulse. The liquid element dV then reaches the conductivity sensor 16 arranged downstream from the dialyzer through the system composed of the hose inlet, the dialyzer and the hose outlet. To accomplish this, the maximum pulse needs time $t_{tot}$, as a result of which the pulse is diffused by the difference in the propagating time of the individual particles and then takes on the shape of the function $g(t-t_{tot})$ shown in FIG. 2b.

The following convolution integral can be formulated for the ratio between the course over time of the dialysate outlet concentration cdo(t) and the dialysate inlet concentration cdi(t):

$$cdo(t) := \int_{t-t_g}^{t+t_g} cdi(t' - t_{tot}) \cdot f(t') \cdot g(t - t') dt'. \quad (4)$$

In the above convolution integral $t_g$ is the length of time that a pulse response on the outlet side requires to decline or rise below half the measuring accuracy from its maximum. For time $t_g$ $$\frac{g(t_g)}{g(0)} \leq \frac{M}{2} \quad (5)$$

is applicable, with M representing the measuring accuracy demanded.

Function f(t) is a correcting factor variable over time that takes the particle loss/gain into account. On the assumption that particle losses or gains in the dialyzer are constant over time, f(t) is constant. In cases where there is no exchange of particles, f(t) equals 1.

The course over time of the dialysate inlet concentration cdi(t) and dialysate outlet concentration cdo(t) can be determined by the conductivity sensors upstream and downstream of the dialyzer. The time $t_g$ can likewise be measured. The pulse response can be unfolded over any optional inlet bolus and so can the resulting Laplace transform. This means, in particular, that no prior, separate measurement to determine the pulse response is required. What is more, the pulse response can be directly derived from the measured data. But the pulse response f(t) can also be determined by prior measurement of the dialysate outlet concentration if a very narrow (ideally, infinitesimal) electrolyte concentration bolus is loaded on the dialysate flowing in the dialyzer by means of the arrangement 22.

The time $t_{tot}$ can be maintained above the maximum correlation function K of the course over time of the dialysate inlet concentration cdi(t) and the dialysate outlet concentration cdo(t) to the point in time t if the function cdi(t) and cdo(t) are reciprocally shifted chronologically around time t, as a result of which the correlation function $K(t_v)$ can be calculated, $$K(t_v) = \frac{\int_0^t (cdi(t') - cdi_{mean}) \cdot (cdo(t' + t_v) - cdo_{mean}) dt'}{\sqrt{\int_0^t (cdi(t') - cdi_{mean})^2 dt' \cdot \int_0^t (cdo(t' + t_v) - cdo_{mean})^2 dt'}} \quad (6)$$

where $cdi_{mean}$ is the mean value of all cdi's and $cdo_{mean}$ is the mean value of all the cdo's.

The pulse response g(t) represents the core of the convolution integral (4) and can therefore be regarded as a weighting function, which indicates what portion of the dialysate outlet concentration cdo(t) at point in time $t'-t_{tot}$ a given value of the dialysate inlet concentration cdi ($t'-t_{tot}$) has, where t' lies in the range ($t-t_g$, $t+t_g$). This weighting makes it possible to determine at any time the dialysate inlet concentration relating to a specific dialysate outlet concentration and, suitably weighted, to convert it to the equivalent dialysate inlet concentration that must have prevailed if the system had been stationary.

The dialysate inlet concentration $cdi_{stat}(t)$ corresponding to a stationary state yields:

$$cdi_{stat}(t) = \int_{t-t_g}^{t+t_g} cdi(t' - t_{tot}) g(t - t') dt' \quad (7)$$

In the case of a first example of an embodiment of the device for determining hemodialysis parameters described in FIG. 1, in particular of the dialysance D, the course of the measurement is predetermined by the control unit as follows:

The control unit 24 sends a control signal to the arrangement 22 for changing the dialysate concentration which then produces a concentrate bolus upstream of the dialyzer 5. The course of the change over time of the dialysate inlet concentration cdi and the dialysate outlet concentration cdo is detected by means of the conductivity sensors 15, 16 whose measurement data is stored in the storage unit 19. The inlet and outlet signals represented by a sequence of discrete measurement values are analyzed in a computer and analyzer unit 21, as a result of which the $t_{tot}$ and $t_g$ are calculated according to the above equations. From the pulse response determined by a prior measurement or predetermined pulse response of the dialyzer and the values of the dialysate inlet concentration cdi, the values of the dialysate inlet concentration $cdi_{stat}(t_1)$ and $cdi_{stat}(t_2)$ corresponding to a stationary state are determined. The dialysance is then calculated in the computer unit according to the following equation:

$$D = Q_d \frac{(cdi_{stat}(t_1) - cdo(t_1)) - (cdi_{stat}(t_2) - cdo(t_2))}{cdi_{stat}(t_1) - cdi_{stat}(t_2)} \qquad (8)$$

In a second example of embodiment of the device described with reference to FIG. 1 the pulse response of the dialyzer 5 is calculated from the course over time of the dialysate inlet concentration cdi(t) and the course over time of the dialysate outlet concentration cdo(t) in the computer and analyzer unit 21 by a Laplace transform. Then the integral over the pulse response of the dialyzer is calculated in the computer and analyzer unit. For this the analyzer and computer unit has an integrator. Moreover, the analyzer and computer unit has a memory in which a (precalibrated) cross-reference table is stored. The table coordinates a specific dialysance for various dialysate flow rates Qd of various values for the integral over the pulse response of the dialyzer. The pulse response T(t, t') of the dialyzer is reproduced in Equation (4) by the product f(t')g(t−t'). The computer and analyzer unit 21 compares the integral over the pulse response of the dialyzer calculated from the dialysate inlet and outlet concentration with the values stored in the memory and then determines the dialysance of the dialyzer.

By means of the method according to the invention not only the dialysance can be determined, but it is also possible to determine additional parameters of the hemodialysis, e.g., the blood inlet concentration, the effective blood water flow and the hematocrit in one continuing measurement during the dialysis. The advantages afforded by the dialysate inlet concentration corresponding to a stationary state come to fruition in all measurement procedures for determining hemodialysis parameters in which physical or chemical characteristic quantities, e.g., substance concentration of the dialysate, are measured in the dialysate path upstream and downstream of the dialyzer.

What is claimed is:

1. A method of determining a hemodialysis parameter during hemodialysis comprising the steps of:
   providing blood to be treated to a blood chamber in a dialyzer, the dialyzer being divided by a semipermeable membrane into the blood chamber and a dialysate chamber;
   providing dialysate to the dialysate chamber through a dialysate path, wherein the dialysate enters the dialysate chamber through a dialysate chamber inlet and exits the dialysate chamber through a dialysate chamber outlet;
   changing a characteristic quantity of the dialysate upstream of the dialysate chamber inlet;
   measuring the characteristic quantity of the dialysate downstream of the dialysate chamber outlet;
   determining a pulse response of the dialyzer by comparing the measurement of the characteristic quantity of the dialysate downstream to the change in the characteristic quantity of the dialysate upstream; and
   determining the hemodialysis parameter using the pulse response.

2. The method of claim 1 wherein the characteristic quantity of the dialysate is a dialysate substance concentration.

3. The method of claim 2 wherein the characteristic quantity of the dialysate is the sodium (Na) concentration.

4. The method of claim 3 wherein sodium concentration is changed by providing a bolus of sodium upstream of the dialysate chamber.

5. The method of claim 4 further comprising a control unit adapted to signal the release of a bolus of sodium and further comprising the step of:
   providing a signal from the control unit causing the release of a bolus of sodium into the dialysate upstream of the dialysate chamber.

6. The method of claim 1 wherein a first measuring device is provided upstream of the dialysate chamber and a second measuring device is provided downstream of the dialysate chamber, wherein the first and second measuring devices measure the characteristic quantity of the dialysate, and further comprising the steps of:
   measuring the characteristic quantity of the dialysate upstream of the dialysate chamber; and
   determining the pulse response of the dialyzer by comparing the measurement of the characteristic quantity of the dialysate upstream of the dialyzer to the measurement of the characteristic quantity of the dialysate downstream of the dialyzer.

7. The method of claim 6 wherein the first and second measuring devices are selected from the group consisting of a conductivity sensor and an optical sensor.

8. The method of claim 6 wherein the characteristic quantity of the dialysate is dialysate temperature, the first and second measuring devices are temperature sensors, and the change in the temperature is provided by a heating device provided in the dialysate path upstream of the dialysate chamber.

9. The method of claim 8 further comprising a control unit adapted to signal the heating arrangement to produce a dialysate temperature surge and further comprising the step of:
   providing a signal from the control unit and thereby causing a temperature surge in the dialysate upstream of the dialysate chamber.

10. The method of claim 6 further comprising the steps of:
    determining a characteristic quantity of the dialysate upstream of the dialysate chamber corresponding to a stationary state, of the quantity ($cdi_{stat}$) using the pulse response of the dialyzer and a characteristic quantity of the dialysate upstream from the dialysate chamber in the following equation:

$$cdi_{stat}(t) = \int_{t-t_g}^{t+t_g} cdi(t' - t_{tot})g(t - t')dt'$$

where t is the length of time for a pulse response downstream of the dialysate chamber to decline or rise below half the measuring accuracy from its maximum, t is a given point in time and g(t−t') is the pulse response representing a weighting function which indicates what portion of the dialysate outlet concentration cdo(t) at point in time ($t-t_{tot}$) a given value of the dialysate inlet concentration $cdi(t'-t_{tot})$ has, where t' lies in the range ($t-t_g$, $t+t_g$) and $t_{tot}$ is the mean propagating time of the change in the characteristic quantity of the dialysate upstream of the dialysate chamber from the dialyzer inlet to the dialyzer outlet; and
   determining the hemodialysis parameter using the characteristic quantity of the dialysate upstream of the dialysate chamber corresponding to a stationary state.

11. The method of claim 10 further comprising the steps of:
    changing the characteristic quantity of the dialysate upstream of the dialysate chamber over a predetermined time interval;

measuring the characteristic quantity of the dialysate downstream of the dialysate chamber at first and second measurement times; and determining the dialysance D of the characteristic quantity of the dialysate by determining the difference between the differences of the characteristic quantity of the dialysate upstream of the dialysate chamber corresponding to a stationary state ($cdi_{stat}$) a and the measured characteristic quantity of the dialysate downstream of the dialysate chamber at the first and second measurement times, dividing by the difference between the characteristic quantity of the dialysate upstream of the dialysate chamber corresponding to a stationary state at the time of the first measurement and the characteristic quantity of the dialysate upstream of the dialysate chamber corresponding to a stationary state at the time of the second measurement, and multiplying by the dialysate flow ($Q_d$).

12. The method of claim 1 further comprising the steps of:
generating an inlet signal from the change in the characteristic quantity of the dialysate upstream of the dialysate chamber;
generating an outlet signal from the measurement of the characteristic quantity of the dialysate downstream of the dialysate chamber;
determining the pulse response using the inlet signal and outlet signal.

13. The method of claim 12 further comprising the steps of:
conveying the inlet signal and outlet signal to a storage unit that stores inlet signals and outlet signals in chronological order; and
conveying the stored inlet signals and outlet signals to a microprocessor, which compares the inlet signals and outlet signals to determine the pulse response and determines the hemodialysis parameter using the pulse response.

14. The method of claim 1 wherein the hemodialysis parameter being determined is the dialysance of the characteristic quantity of the dialysate and further comprising the steps of:
determining the integral of the pulse response; and
comparing the integral over the pulse response to predetermined values of the integral over the pulse response corresponding to specific dialysance values for the characteristic quantity of the dialysate.

15. A method of determining a hemodialysis parameter during hemodialysis comprising the steps of:
providing blood to be treated to a blood chamber in a dialyzer, the dialyzer being divided by a semipermeable membrane into the blood chamber and a dialysate chamber;
providing dialysate to the dialysate chamber through a dialysate path, wherein the dialysate enters the dialysate chamber through a dialysate chamber inlet and exits the dialysate chamber through a dialysate chamber outlet;
providing a pulse function upstream of the dialysate chamber inlet;
generating an inlet signal from the pulse function provided upstream of the dialysate chamber inlet;
generating an outlet signal from the pulse function by measuring the downstream response of the dialyzer to the pulse function;
determining a pulse response of the dialyzer to the pulse function using the inlet signal and outlet signal; and
determining the hemodialysis parameter using the pulse response.

16. A device for determining a hemodialysis parameter comprising (a) a dialyzer divided by a semipermeable membrane into a blood chamber having an inlet and an outlet and a dialysate chamber having an inlet and an outlet, (b) an extracorporeal blood circulation unit connected to the blood chamber for providing blood to the blood chamber, (c) a dialysate path connected to the dialysate chamber for providing dialysate to the dialysate chamber, (d) means for changing a characteristic quantity of the dialysate in the dialysate path upstream from the dialysate chamber in a predetermined time interval and generating an inlet signal for the change of the quantity (e) means for measuring the characteristic quantity of the dialysate in the dialysate path downstream from the dialysate chamber and generating an outlet signal from the measured quantity, (f) a storage unit adapted to receive and store the inlet signal and outlet signal in chronological sequence, and (g) a microprocessor connected to the storage unit that is adapted for determining the hemodialysis parameter, wherein the microprocessor determines a pulse response of the dialyzer by comparing the inlet signal and outlet signal and determines the hemodialysis parameter using the pulse response.

17. The device of claim 16 further comprising a means of measuring the characteristic quantity of the dialysate upstream of the dialysate chamber and generating an inlet signal from the change in the characteristic quantity of the dialysate upstream of the dialysate chamber.

18. The device according to claim 17 wherein the microprocessor is adapted to determine the characteristic quantity of the dialysate upstream of the dialysate chamber corresponding to a stationary state ($cdi_{stat}$) using the pulse response of the dialyzer, the measured values of the characteristic quantity upstream of the dialysate chamber and the measured values for the characteristic quantity downstream of the dialysate chamber, and wherein the hemodialysis parameter is determined by comparing the calculated value for $cdi_{stat}$ to known values of the hemodialysis parameter corresponding to the calculated $cdi_{stat}$ value.

19. The device according to claim 16 wherein the microprocessor further comprises an integrator for determining the integral of the pulse response of the dialyzer and a means for determining the dialysance D of the hemodialysis parameter by comparing the calculated integral of the pulse response to known dialysance values corresponding to the calculated value.

20. The device of claim 16 wherein the means for changing the characteristic quantity of the dialysate upstream of the dialysate chamber is a means for changing the substance concentration.

21. The device of claim 20 wherein the means for changing the substance concentration is a means for providing a bolus of sodium (Na) to the dialysate.

22. The device of claim 20 wherein the means for measuring the characteristic quantity of the dialysate upstream and the means for measuring the characteristic quantity of the dialysate downstream of the dialysate chamber are selected from the group consisting of: conductivity sensors and optical sensors.

23. The device of claim 16 wherein the means for changing the characteristic quantity of the dialysate upstream of the dialysate chamber is a means for changing the temperature of the dialysate.

24. The device of claim 23 wherein the means for measuring the characteristic quantity of the dialysate upstream and the means for measuring the characteristic quantity of the dialysate downstream of the dialysate chamber are thermometers.

* * * * *